(12) United States Patent
Amthor et al.

(10) Patent No.: US 11,574,728 B2
(45) Date of Patent: Feb. 7, 2023

(54) METHOD FOR ENABLING MAGNETIC RESONANCE IMAGING OF A SUBJECT

(71) Applicant: KONINKLIJKE PHILIPS N.V., Eindhoven (NL)

(72) Inventors: Thomas Erik Amthor, Hamburg (DE); Liqin Wang, Belle Mead, NJ (US); Chenguang Zhao, Suzhou (CN); Joachim Dieter Schmidt, Hamburg (DE); Jorn Borgert, Hamburg (DE); Yajing Zhang, Suzhou (CN); Ingmar Graesslin, Boenningstedt (DE); Tanja Nordhoff, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 24 days.

(21) Appl. No.: 17/254,321

(22) PCT Filed: Jun. 19, 2019

(86) PCT No.: PCT/EP2019/066150
§ 371 (c)(1),
(2) Date: Dec. 21, 2020

(87) PCT Pub. No.: WO2019/243400
PCT Pub. Date: Dec. 26, 2019

(65) Prior Publication Data
US 2021/0118554 A1    Apr. 22, 2021

(30) Foreign Application Priority Data

Jun. 22, 2018  (WO) ................ PCT/CN2018/092476
Jul. 24, 2018   (EP) ..................................... 18185117

(51) Int. Cl.
*G01V 3/00*    (2006.01)
*G16H 30/40*   (2018.01)
(Continued)

(52) U.S. Cl.
CPC .......... *G16H 30/40* (2018.01); *G01R 33/543* (2013.01); *G06F 16/2379* (2019.01); *G16H 50/20* (2018.01)

(58) Field of Classification Search
CPC .... G01R 33/307; G01R 33/30; G01R 33/302; G01R 33/305; G01N 24/08
(Continued)

(56) References Cited

U.S. PATENT DOCUMENTS 10,754,665 B2    8/2020  Grant et al.
2012/0190962 A1  7/2012  Glaser-Seidnitzer et al.
(Continued)

FOREIGN PATENT DOCUMENTS

CN    101204326 B  * 12/2012 ........... G01R 33/481
CN    103533343 B  *  5/2015 ........... G06T 1/0028
(Continued)

OTHER PUBLICATIONS

New study reveals why many MRI scans are delayed. Wayne Forrest, 2017, AuntMinnie.com.
(Continued)

*Primary Examiner* — Walter L Lindsay, Jr.
*Assistant Examiner* — Frederick Wenderoth (57) ABSTRACT

The present disclosure relates to a medical imaging method for enabling magnetic resonance imaging of a subject (318) using a set of imaging parameters of imaging protocols, the method comprising: receiving information related to the subject; using a predefined machine learning model for suggesting at least one imaging protocol for the received information, wherein the imaging protocol comprises at least part of the set of imaging parameters and associated values; providing the imaging protocol.

15 Claims, 4 Drawing Sheets

(51) Int. Cl.
*G16H 50/20* (2018.01)
*G06F 16/23* (2019.01)
*G01R 33/54* (2006.01)

(58) Field of Classification Search
USPC .......................................................... 324/322
See application file for complete search history.

(56) References Cited

U.S. PATENT DOCUMENTS

| | | |
|---|---|---|
| 2013/0265044 A1 | 10/2013 | Senegas et al. |
| 2013/0311472 A1 | 11/2013 | Cohen-Solal et al. |
| 2014/0088984 A1 | 3/2014 | Oh et al. |
| 2015/0081315 A1 | 3/2015 | Baker |
| 2015/0089523 A1* | 3/2015 | Volovich ............... H04H 60/66 725/14 |
| 2015/0161329 A1* | 6/2015 | Mabotuwana ......... G16H 10/60 705/3 |
| 2015/0199478 A1 | 7/2015 | Bhatia et al. |
| 2019/0026128 A1 | 1/2019 | Grant et al. |

FOREIGN PATENT DOCUMENTS

| | | | | |
|---|---|---|---|---|
| DE | 102016209032 B3 * | 9/2017 | ............. | A61B 5/024 |
| EP | 1522933 A2 * | 4/2005 | ......... | G06F 16/3329 |
| WO | WO-2013075127 A1 * | 5/2013 | ......... | G06F 16/5838 |

OTHER PUBLICATIONS

Michalski, R. S., Carbonell, J. G., Mitchell T. M., Machine learning: An artificial intelligence approach, Journal of Mathematical Psychology, 1983.

M Reczko, DA Karras, BG Mertzios, D Graveron-Demilly, DV Ormondt. Improved MR image reconstruction from sparsely sampled scans based on neural networks. Pattern Recognition Letters. 2001, 22 (1): 35-46.

M Gomathi, P Thangaraj. A computer aided diagnosis system for lung cancer detection using support vector machine Americal Journal of Applied Sciences 7(12) 2010.

International Search Report and Written Opinion from PCT/EP2019/066150 dated Sep. 26, 2019.

* cited by examiner

METHOD FOR ENABLING MAGNETIC RESONANCE IMAGING OF A SUBJECT

CROSS REFERENCE TO RELATED APPLICATIONS

This application is a U.S. national phase application of International Application No. PCT/EP2019/066150 filed on Jun. 19, 2019, which claims the benefit of PCT/CN2018/092476 filed on Jun. 22, 2018 and EP Application Serial No. 18185117.1 filed on Jul. 24, 2018, which are incorporated herein by reference.

FIELD OF THE INVENTION

The invention relates to scanning imaging systems, in particular to a method for enabling magnetic resonance imaging (MRI) of a subject.

BACKGROUND OF THE INVENTION

For magnetic resonance imaging, typically many pre-configured imaging protocols ("Examcards") are installed on the imaging systems, usually adapted by the customers to their specific needs. When a new patient is arriving for an examination, a technologist will have to select a matching Examcard to be used from a large database. In many cases, the Examcard then needs to be adapted to the patient, the clinical question, or the preferences of the referring physician. This process is time-consuming, especially for less-trained staff, and a non-ideal choice may lead to non-ideal diagnostic information or unnecessary scans. The time required to select and tune the Examcard is especially relevant in emergency situations, where often minutes or seconds count to perform a diagnosis and choose a treatment.

The US patent application US2015/0199478 refers to CT/x-ray applications and examples and mentions MRI only as one of many imaging techniques. The known method is limited to identify a set of imaging parameters for each individual patient that is likely to produce an image of high quality according to a calculated image quality score.

SUMMARY OF THE INVENTION

Various embodiments provide for a method for enabling magnetic resonance imaging of a subject, medical analysis system, and computer program product, as described by the subject matter of the independent claims. Advantageous embodiments are described in the dependent claims.

The manual process of selecting the best-suited Examcard for an imaging procedure is time-consuming, especially for less-trained staff. In many cases, the Examcard needs to be adjusted to the patient or the clinical question manually before starting the exam. Non-ideal choices or settings may lead to non-ideal diagnostic information or unnecessary scans. This is especially problematic in emergency situations. The present method and system overcomes these problems by choosing and proposing an imaging protocol based on prior knowledge about the clinical question, the patient's condition, and the referring physician. The system reduces the time spent on protocol selection and tuning and may also lead to a shorter overall scan time because no unnecessary scans are performed, better reproducibility of results, and therefore to an increase of diagnostic quality.

In one aspect, the invention relates to a medical imaging method for enabling magnetic resonance imaging of a subject using a set of representative parameters of imaging protocols. The method comprises: receiving information related to the subject for a specific clinical question; using a predefined machine learning model for suggesting at least one imaging protocol for the received information, wherein the imaging protocol comprises at least part of the set of imaging parameters and associated values; providing the imaging protocol.

An MR examination typically takes a long time, consists of many image acquisitions yielding different contrasts, and includes some other tasks, such as patient communication, retakes, protocol and geometry adaptation, contrast agent injection, complex breath hold instructions, etc. A simple image quality score is therefore not sufficient to describe the "quality" of the examination. For example, when a patient is unable to lie still, the operator may decide to choose a completely different protocol that leads to a different kind of images but still allows to the required diagnosis. Furthermore, the quality of a protocol selection is also reflected in the efficiency (speed) of the examination, the number of rescans and other issues, and in the satisfaction of the patient and staff. These imaging protocol may be represented by representative parameters such as its image contrasts, geometry settings, number and order of image acquisitions including delays, susceptibility to motion, i.e. the entries in the Exam Card qualify as representative for the image protocol.

For all of the above reasons, the present invention does not (solely) use image quality scores as training labels. A "good" protocol is rather identified by what was finally chosen by the operator for the specific patient, i.e. the automated selection of Exam Cards is reflecting what experienced staff with full knowledge about the patient would have done. This is learned from historic workflows: When, after a few unsuccessful image acquisitions, an operator decided to try a different contrast mechanism or changed the imaging parameters and then stored the final images in the PACS, the final settings can be assumed to be the most suited.

The present invention is therefore trained mainly on successful selection of the image protocol s of historic data and on workflow issues (retakes, delays, too much communication) detected from historic modality log files.

In addition, there may also be an optional direct operator feedback loop included in the present invention that allows the operator to specify a reason for a specific manual choice of protocol. In this way, the system continuously learns from the experience of the operators to propose the best suited Exam Card or parameter settings.

The implementation of the present invention features the clinical question and referral information, workflow issues before best settings in addition to patient information. The machine learning model outputs on the basis of the clinical question etc. optimal technical settings (e.g. Exam Card and imaging parameters, and solutions for remaining workflow issues. The invention is outputs learned technical settings as result of forward ML implementation.

If the provided imaging protocol does not fulfil a predefined selection criterion, a warning may be output. The warning may indicate that "the parameter setting likely to give bad image quality", or the unreasonable setting would not trigger scan start. The selection criterion may for example require that the image quality of images that can be obtained using the provided imaging protocol is higher than a predefined threshold.

For example, the machine learning model may be configured to suggest multiple imaging protocols each associated with a probability of success. The probability of success may for example be the probability of getting a good image quality with the associated imaging protocol.

The term "machine learning" refers to a computer algorithm used to extract useful information from training data by building probabilistic models (referred to as machine learning or learned models) in an automated way. The machine learning may be performed using one or more learning algorithms such as linear regression, K-means, classification algorithm, reinforcement algorithm etc. A "model" may for example be an equation or set of rules that makes it possible to predict an unmeasured value (e.g. which configuration corresponds to a given operating condition) from other, known values and/or to predict or select an action to maximize a future reward or minimize a future penalty. According to one embodiment, the machine learning model is a deep learning model.

The term "imaging protocol" or "protocol" refers to a set of technical settings or parameters of the imaging modalities to produce all the images (e.g. MR images) required for an examination.

MR operation is a complex procedure. There may be hundreds of pulses sequences to generate, different image contracts, proton density, T1 weighting, diffusion, perfusion, cerebral blood flow etc. Additionally, for each sequence, there are at least tens of parameters for the operator to play with to obtain satisfactory clinical images that are suitable for diagnosis. Furthermore, it is quite a common request for the operator to fine tune and optimize the sequence parameters for different anatomies. As a result, to get the first time right clinical images is largely dependent upon the training and experiences of the scanner operators, and the failure rate of MR scans due to improper study protocol may be around 5%, which leads to delayed scans and increased cost in running the system. The present method and system may overcome this problem. The present method may enable to find the optimal configuration set for an imaging protocol based on the subject related information.

The present disclosure may enable to automate the operation of the magnetic resonance imaging system. This may reduce the need for operator intervention for the configuration of the MRI system.

According to one embodiment, the method further comprises: receiving a training set indicative of imaging protocols in association with respective subject information; training a predefined machine learning algorithm using the training set, thereby generating the machine learning model. For example, different machine learning algorithms may be applied based on the available amount of data of the training set and the available processing resources. The training set may for example be collected from multiple MRI systems and/or other databases comprising hospital databases or practice network (HIS, RIS, PACS) and modality log files, imaging guidelines, imaging appropriateness criteria, and manual data entry. for example, the training set may include information about the protocol settings used, other technical settings, the clinical question, the patient's background and condition, and the radiology report generated after the examination. The machine learning algorithm may be trained on the collected data to predict which protocol to use for a specific patient and clinical question.

This may increase the accuracy of the generated model. The training may for example be performed on a periodic basis. This may enable up-to-date models for an accurate prediction of the imaging protocols.

According to one embodiment, the method further comprises generating the training set comprising collecting data from at least one data source, and extracting from the collected data the imaging protocols and associated subject information, wherein the data source comprises at least one of log files of MRI systems and user reports indicative of imaging protocols and subjects imaged using said imaging protocols. This embodiment may enable a rich training set that can be used to provide reliable and accurate prediction models.

According to one embodiment, the training set comprises simulation data that is obtained from a simulation of magnetic resonance imaging of subjects. The simulation may enable to simulate as much data as needed and for different configurations. This may enable to obtain a large training set which may further increase the accuracy and reliability of the present method.

For example, the imaging system may be pre-trained by a technologist simulating examination cases. A number of either simulated or historical datasets including clinical question, referral and patient information are provided to the technologist, who then selects and adjusts an imaging protocol as it would have been done for a real examination. The system is then trained with these simulated examinations.

According to one embodiment, the method further comprises repeating the suggesting step for other received subject information, and updating the training set using the suggested imaging protocols and the received subject information and repeating the training of the machine learning algorithm using the updated training set. The training set is updated with the suggested imaging protocols that have been further been selected for usage for imaging or that have a difference with predefined reference protocol that is smaller than a predefined threshold. The predefined reference imaging protocol may be the imaging protocol that has been used for the examination for which the suggested imaging protocol has been predicted or may be a predefined imaging protocol e.g. of an Examcard. This may enable a feedback system for improving the content of the training set. For example a technical system or user interface may be used to present the suggested imaging protocol or protocols to the operator. The feedback system may be configured to collect information about the reason (e.g. image quality) for the operator's choice (to be fed back to the training data). This may further increase the accuracy of the predictions performed by the generated models.

In one example, the difference between the suggested imaging protocol and the predefined reference protocol is used to produce a real-time alert when the performed examination (e.g. the used imaging protocol) differs by more than a certain amount from the proposed imaging protocol. Alerts can be shown on a scanner console or any other computer screen, can be monitored by a central data processing unit, or can be indicated by a visual or audible alarm. Real-time alarms are useful to make staff aware of a deviation from standard operating procedures (SOP) and may be part of a quality assurance system.

According to one embodiment, each imaging protocol of the training set is associated with a quality score indicative of the quality of images that can be obtained from an imaging using the each imaging protocol, wherein the training set comprises the quality scores. Labeling the imaging protocols by the image quality scores may further increase the accuracy of the predictions performed by the generated models as the provided imagine protocol may be the one predicted for a predefined subject related information and a suited image quality.

According to one embodiment, the quality score comprises at least one of: image quality of the obtainable images, the number of user interventions when using the imaging protocol, number of MR repeat scans when using the imaging protocol, delays and idle times and their distribution when using the imaging protocol.

According to one embodiment, wherein a protocol database (e.g. Examcard database) comprises imaging protocols, the method further comprises determining the difference between the provided imaging protocol and a predefined reference imaging protocol of a protocol database, and updating the protocol database based on the determined difference.

For example, the difference may be between the provided imaging protocol and the imaging protocol that is used for examination or between the provided protocol and the closest match from the pre-installed Examcards. This can be implemented using either the Examcards stored locally on the imaging systems or using a central Examcard database. A difference measure can be based on the individual scan parameters of the imaging protocol and/or on the order and type of image contrasts and geometries. Statistical analysis of this difference measure may allow to monitor the training progress of the system or to identify examination types for which no adequate Examcard is available in the database. This information can be used to offer a service to the customer by proposing new pre-installed Examcards to be added or optimization of existing Examcards to be better aligned with clinical requirements.

According to one embodiment, the subject related information comprises a description of the subject and/or clinical use case of the subject.

The information related to the subject or the subject related information comprises records of data of multiple attributes each describing a property related to the subject. A first set of attributes of the multiple attributes comprises information descriptive of the subject comprising at least the clinical question of the subject, the anatomy to be imaged and behavioral information of the subject. A second set of attributes of the multiple attributes comprises referral information specifying a referral regarding the subject by multiple referring sources comprising at least an indication of the current and past medical status of the subject and symptoms. The values of the attributes may be interdependent e.g. the value of one attribute may not be changed without performing a multidimensional analysis of the interdependent attributes.

For example, a patient scheduled for a brain tumor examination is known to be difficult to communicate with. This may be provided as part of the subject related information. The subject related information may further comprise referral information of a referring physician. The referral information may for example indicate referring physician's preferences for performing an imaging of a subject. From this information and the patient's medical and imaging record, the machine learning model selects an imaging protocol containing mostly motion-insensitive scans that still allow for the detection and localization of lesions in the brain. Since the referring physician is known to expect an image of a specific slice geometry and contrast type, this preference is also considered in the protocol generation.

According to one embodiment, the suggesting comprises predicting the imaging protocol using the subject information.

According to one embodiment, the method further comprises receiving a set of imaging parameters, the suggesting comprising: predicting a quality score for the received set of imaging parameters and the subject information, wherein the suggested parameters of the imaging protocol are the received set of parameters if the predicted quality score is higher than a predefined threshold; or adjusting the received set of parameters if the predicted quality score is smaller than the predefined threshold, wherein the suggested parameters of the imaging protocol are the adjusted parameters. The machine learning model may for example receive as input the parameters and also the subject related information any may output an IQ value.

For example, in the application stage, the machine learning model may evaluate the IQ condition according to the input scan parameter vector, before the actual scan occurs. The operator leverages the predicted information which helps to finalize a set of scan parameters that yields acceptable IQ, and the actual scan could be performed first-time-right. The machine learning model may further suggest an optimized scan parameter set that ensures acceptable IQ.

In another aspect, the invention relates to a computer program product comprising machine executable instructions for execution by a processor, wherein execution of the machine executable instructions causes the processor to the methods of any of the preceding embodiments.

In another aspect, the invention relates to a medical analysis system (or medical control system) comprising: a memory containing machine executable instructions; and a processor for controlling the medical analysis system, wherein execution of the machine executable instructions causes the medical imaging system to:

receive information related to a subject;

use a predefined machine learning model for suggesting at least one imaging protocol for the received information, wherein the imaging protocol comprises at least part of the set of parameters and associated values;

provide the imaging protocol.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function. Elements which have been discussed previously will not necessarily be discussed in later figures if the function is equivalent.

Various structures, systems and devices are schematically depicted in the figures for purposes of explanation only and so as to not obscure the present invention with details that are well known to those skilled in the art. Nevertheless, the attached figures are included to describe and explain illustrative examples of the disclosed subject matter.

Figure 1:
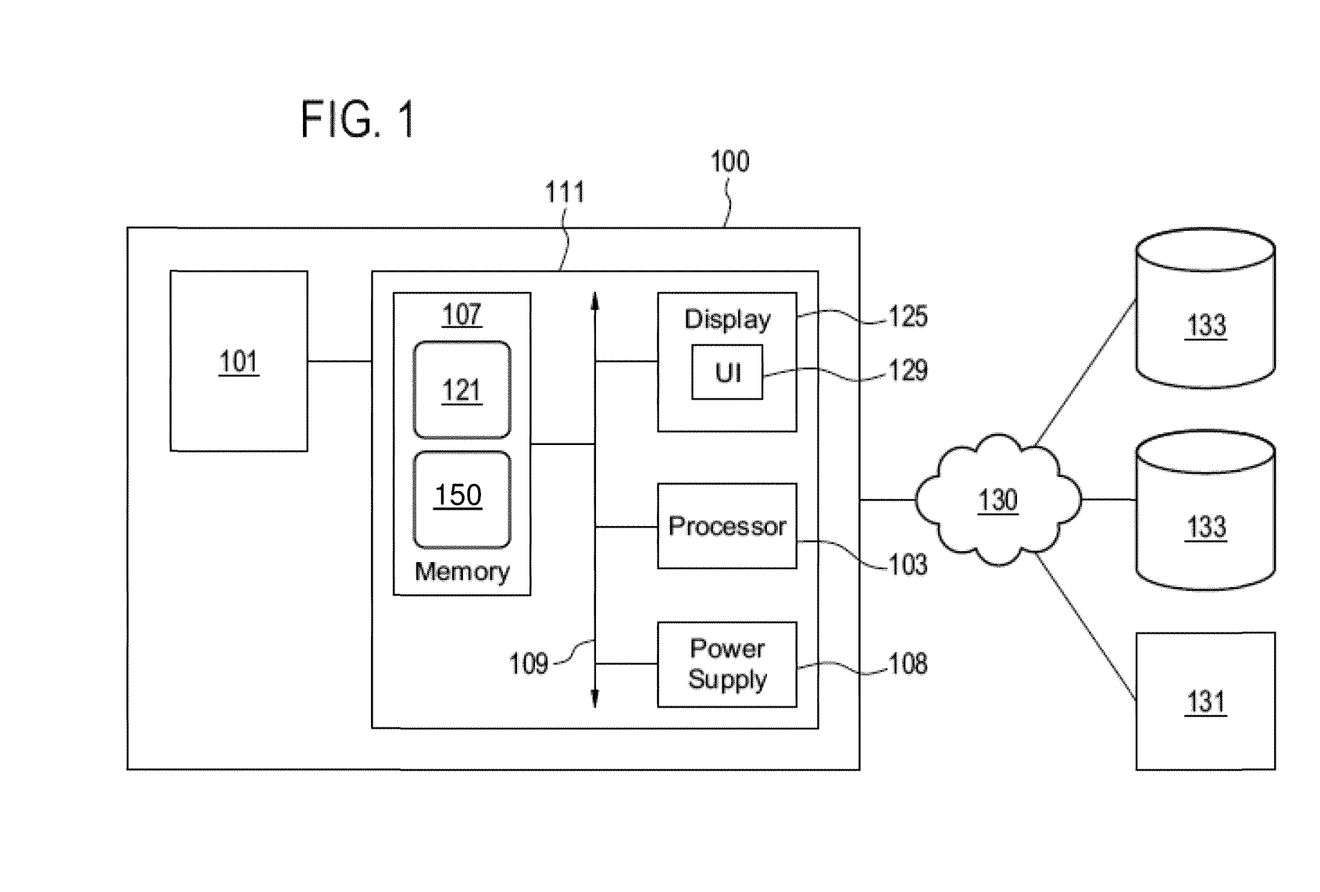
FIG. 1 is a schematic diagram of a medical analysis system.

FIG. 1 is a schematic diagram of a medical analysis system 100. The medical analysis system 100 comprises a control system 111 that is configured to connect to a scanning imaging system (or acquisition component) 101. The control system 111 comprises a processor 103, a memory 107 each capable of communicating with one or more components of the medical system 100. For example, components of the control system 111 are coupled to a bidirectional system bus 109.

It will be appreciated that the methods described herein are at least partly non-interactive, and automated by way of computerized systems. For example, these methods can further be implemented in software 121, (including firmware), hardware, or a combination thereof. In exemplary embodiments, the methods described herein are implemented in software, as an executable program, and is executed by a special or general-purpose digital computer, such as a personal computer, workstation, minicomputer, or mainframe computer.

The processor 103 is a hardware device for executing software, particularly that stored in memory 107. The processor 103 can be any custom made or commercially available processor, a central processing unit (CPU), an auxiliary processor among several processors associated with the control system 111, a semiconductor based microprocessor (in the form of a microchip or chip set), a microprocessor, or generally any device for executing software instructions. The processor 103 may control the operation of the scanning imaging system 101.

The memory 107 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM). Note that the memory 107 can have a distributed architecture, where various components are situated remote from one another, but can be accessed by the processor 103. Memory 107 may store an instruction or data related to at least one other constituent element of the medical system 100.

The control system 111 may further comprise a display device 125 which displays characters and images and the like e.g. on a user interface 129. The display device 125 may be a touch screen display device.

The medical analysis system 100 may further comprise a power supply 108 for powering the medical analysis system 100. The power supply 108 may for example be a battery or an external source of power, such as electricity supplied by a standard AC outlet.

The scanning imaging system 101 may comprise at least one of MRI, CT and PET-CT imagers. The control system 111 and the scanning imaging system 101 may or may not be an integral part. In other terms, the control system 111 may or may not be external to the scanning imaging system 101.

The scanning imaging system 101 comprises components that may be controlled by the processor 103 in order to configure the scanning imaging system 101 to provide image data to the control system 111. The configuration of the scanning imaging system 101 may enable the operation of the scanning imaging system 101. The operation of the scanning imaging system 101 may for example be automatic. FIG. 3 shows example of components of the scanning imaging system 101 being an MRI system.

The connection between the control system 111 and the scanning imaging system 101 may for example comprise a BUS Ethernet connection, WAN connection, Internet connection etc.

In one example, the scanning imaging system 101 may be configured to provide output data such as images in response to a specified measurement. The control system 111 may be configured to receive data such as survey image data from the MRI scanning imaging system 101. For example, the processor 103 may be adapted to receive information (automatically or upon request) from the scanning imaging system 101 in a compatible digital form so that such information may be displayed on the display device 125. Such information may include operating parameters, alarm notifications, and other information related to the use, operation and function of the scanning imaging system 101.

The medical analysis system 100 may be configured to communicate via a network 130 with other scanning imaging systems 131 and/or databases 133. The network 130 comprises for example a wireless local area network (WLAN) connection, WAN (Wide Area Network) connection LAN (Local Area Network) connection or a combination thereof. The databases 133 may comprise information relates to patients, scanning imaging systems, anatomies, scan geometries, scan parameters, scans etc. The databases 133 may for example comprise an EMR database comprising patients' EMR, Radiology Information System database, medical image database, PACS, Hospital Information System database and/or other databases comparing data that can be used for planning a scan geometry. The databases 133 may for example comprise training sets used for generating machine learning models. Additionally or alternatively the training sets may be stored in a local storage (e.g. disk storage or memory) of the control system 111.

The memory 107 may further comprise an artificial intelligence (AI) component 150 (also referred to as machine-learning module). The AI component 150 may or may not be part of software component 121. The AI component 150 may be configured for automatically determining or suggesting, by a machine learning model, at least one imaging protocol based on received input information. The received input information may for example be related to the subject to be scanned by the scanning imaging system 101 (e.g. a MRI system). The suggested imaging protocol may comprise a set of imaging parameters and associated values or range of values.

The AI component 150 may be configured to perform machine learning on training sets in order to generate one or more machine learning models for suggesting the imaging protocol based on information related to the subject to be scanned or imaged. The AI component 150 may be configured to use different machine learning algorithms. The generated machine learning models may be stored in a storage are such as memory 107 of the control system 111.

The AI component 150 may for example be configured to generate control signals for configuring the scanning imaging system 101 in accordance with the determined or suggested imaging protocol.

Figure 2:
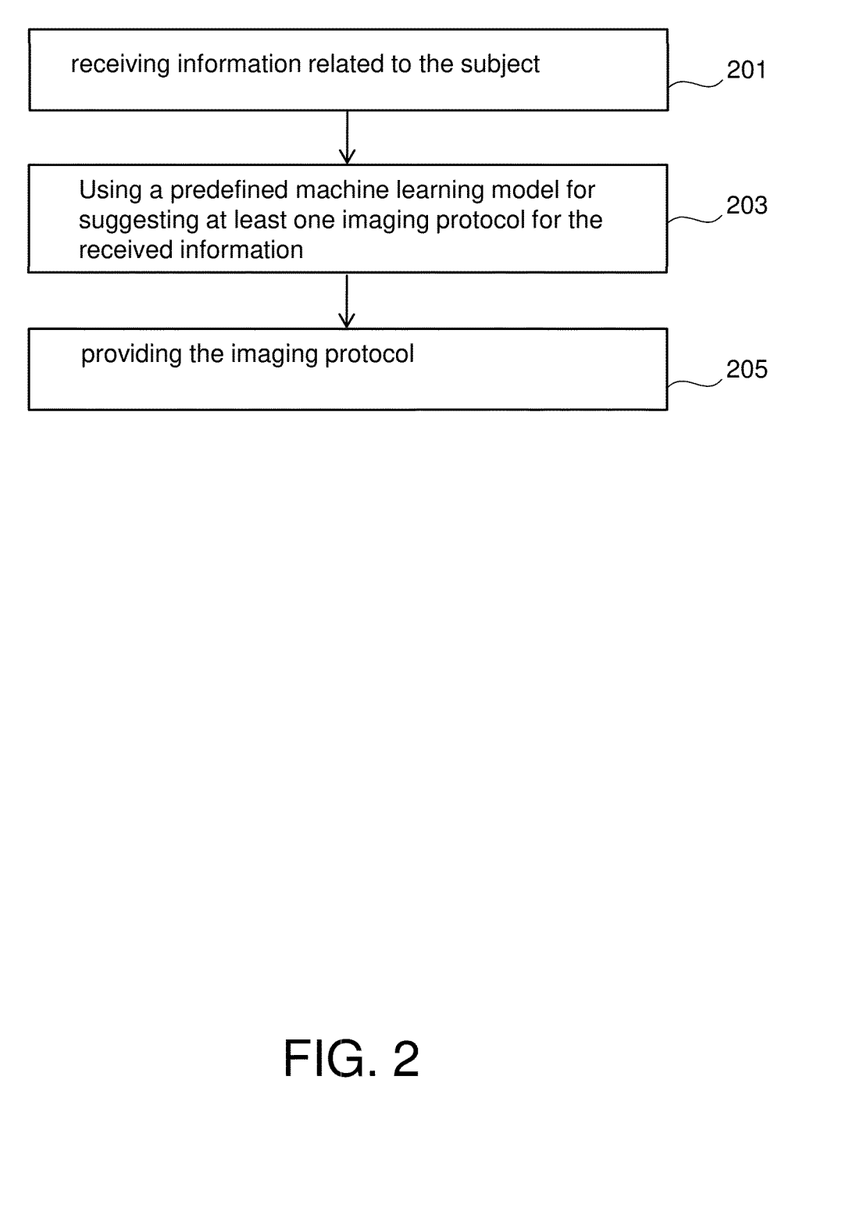
FIG. 2 is a flowchart of a method for enabling magnetic resonance imaging of a subject.

FIG. 2 is a flowchart of a method for enabling magnetic resonance imaging of a subject using a set of imaging parameters of imaging protocols. An imaging protocol may for example be a magnetic resonance imaging protocol.

Figure 3A:
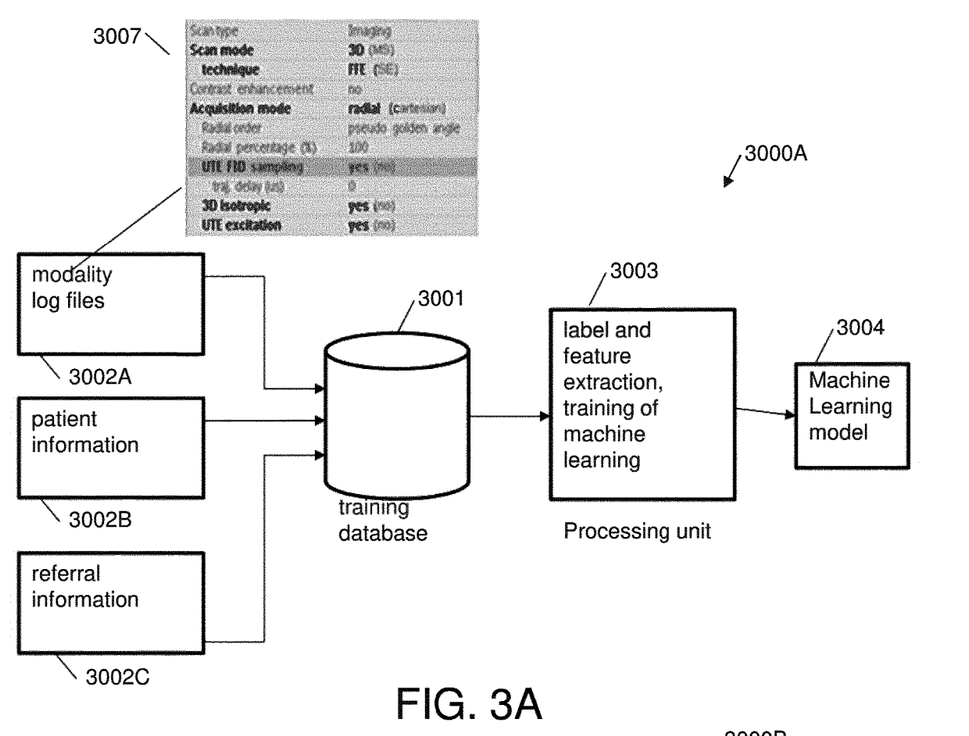
FIG. 3A depicts a block diagram of a training system for training a machine learning algorithm.
Figure 3B:
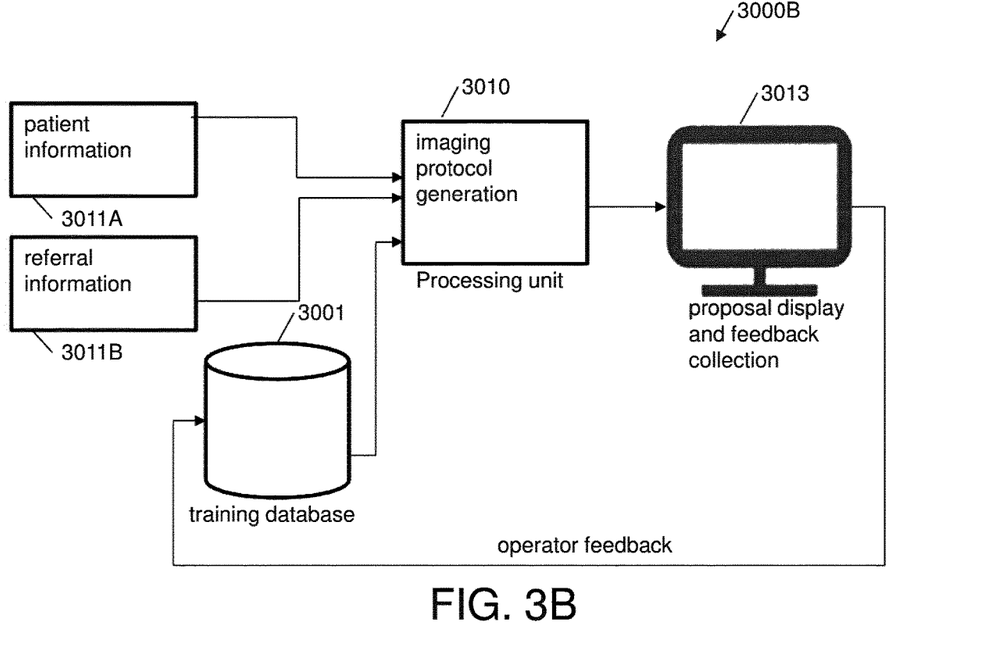
FIG. 3B depicts a block diagram of an application system for providing imaging protocols.

In step 201, subject related information may be received. The subject related information comprises a description of the subject and/or clinical use case of the subject. For example, a predefined machine learning model may receive as input the subject related information. FIGS. 3A-B provide example of subject information.

In step 203, the predefined machine learning model may be used for suggesting at least one imaging protocol for the received information. The imaging protocol comprises at least part of the set of imaging parameters and associated values or range of values. This may enable to integrate the machine learning capability to MR scan parameter optimization process.

In one example, the image quality may be used as well. For example, for each sequence and anatomy, given the scan parameters and a score of the image quality, the machine learning model is trained to find the optimized parameters set to generate the acceptable image quality. This may help to increase the success rate of MR scans, which is the fundamental requirement for further data processing.

In step 205, the imaging protocol may be provided. For example, the imaging protocol may be used to automatically control e.g. the MRI system, for acquiring data in accordance with the parameters of the suggested imaging protocol. Steps 201-205 may automatically be executed.

In one example, a list of proposed imaging protocols may be built containing not only individually provided imaging protocols (of step 205), but also the closest matches of pre-defined protocols e.g. of Examcards stored on the system. In another example, an operator can choose to store the provided protocol in the database of pre-defined Examcards.

FIG. 3A depicts a block diagram of a training system 3000A for training a machine learning algorithm. Using the training system 3000A, data from a variety of historical data sets is collected, features and labels are extracted and the machine learning algorithm is trained.

The training system 3000A comprises a training database 3001. The training database 3001 comprises historical data that is collected from different sources 3002A-C to train the machine learning algorithm. The sources 3002A-C may for example comprise log files 3002A of one or more MRI systems, patient information 3002B and referral information 3002C. For example, the collected data may include, for each examination:

predefined protocol settings (e.g. which are encoded in Examcards of MRI systems) used for the examinations (e.g. obtained from log files of MRI systems). FIG. 3A shows an example of protocol settings as indicated by the parameter listing 3007. The settings may for example indicate parameters that define a pulse sequence such as time to echo (TE), time to repetition (TR), flip angle, field of view and matrix size, inversion pulse(s), spoiler gradient(s) (crusher gradients), echo train length (ETL), the spatial acquisition of k-space, 3D acquisition or 2D acquisition or multiple overlapping slab acquisition, post contrast imaging with gadolinium contrast agents and/or diffusion weighting (b values).

changes to the technical settings or imaging protocols performed during the examination (as obtained from the log files).

workflow information, such as delays, repetitions of tasks, duration of the individual steps of the imaging procedure (as obtained from the log files)

patient demographic information (e.g. obtained from hospital or practice network databases).

patient health status information, including disabilities, precautions to be considered for the examination (e.g. obtained from hospital or practice network databases).

patient social information, including cooperativity, languages spoken (e.g. obtained from hospital or practice network databases).

clinical question from referral (e.g. obtained from hospital or practice network databases).

referring physician (e.g. obtained from hospital or practice network databases)

information about the hospital's or practice's standard operating procedures (SOP).

Training the machine learning algorithm on such a variety of data allows the algorithm to consider, e.g., the referring physician's preferences, the probability for motion artefacts in the images based on the patient's condition, the exact clinical question (e.g. if this a re-scan for disease progression monitoring, some scans may be left out or added as compared to first-time diagnostic imaging). Since the learning is based on historical data in combination with the information about the actually performed procedures, all of these considerations will be learned implicitly by the model.

Using the collected data, labels and features may be extracted by a processing unit 3003. The extracted labels and features may be used to train a machine learning algorithm. The extracted features and labels may be the training set. The machine learning algorithm may be a neural network algorithm, decision trees algorithm, support vector machines algorithm, k-nearest-neighbors algorithm etc. The training of the machine learning algorithm by the processing unit 3003 results in a machine learning model 3004 as illustrated in FIG. 3A. The machine learning algorithm may be a classification type or regression type algorithm. The machine leaning model that is generated by the classification type algorithm may be configured to predict or provide one out of a plurality of choices. The machine leaning model that is generated by the regression type algorithm may provide multiple choices and probabilities for each of the choices. The latter type may be used to propose not a single protocol, but a selection of protocols, ordered by probability of appropriateness or of success.

In one example, the extracted labels may comprise subject information (e.g. an indication of a clinical scan) and the extracted associated features comprise imaging protocols (an imaging protocol may be defined by a respective parameter set). For example, for each clinical scan, parameter settings may be recorded and said recorded data is then collected in order to be processed for defining the training set. This may enable that in the machine learning training stage, a large set of MR scan cases with parameter sets and corresponding subject related information are employed to teach the machine learning model 3004 the implicit logic.

In another example, the extracted labels may further comprise an IQ score indicative of the image quality of the images obtainable by the associated features e.g. imaging protocol. For example, for each clinical scan, parameter settings may be recorded, and record the image quality score (e.g. as evaluated by a radiologist, e.g. a score from 1 to 5).

The IQ score may be given either implicitly or explicitly. Implicit IQ score is generated by tracking the usage of the images. For example, if the image is adopted by radiologists to create a diagnostic report, the IQ of the image will be marked as acceptable. If the image is otherwise ignored by radiologists, the IQ is recognized as not acceptable. Radiologists can also explicitly score the image as acceptable or not, or by giving a quantitative number for the IQ. The correspondence between the sequence parameter set and IQ score is to be used as the training guidance. The target of the machine learning module may be to learn for each sequence at each anatomy an optimized parameter set that is supposed to give the first time right IQ. For example, one sequence may contain a parameter set with a lot of parameters and the parameter set may decide or define the MR signal of the sequence. This may enable that, in the machine learning training stage, a large set of MR scan cases with parameter sets and corresponding IQ scores and subject information are employed to teach the machine learning model 3004 the implicit logic. Each parameter set may be organized as a scan parameter vector, and the machine learning model gains the capability to distinguish a scan parameter vector that yields good image from that with bad image.

FIG. 3B depicts a block diagram of an application system 3000B for providing imaging protocols. For example, when a patient is to be examined, the generated machine learning model (e.g. of FIG. 3A) is used to predict a suited imaging protocol based on subject related data such as patient and referral data and to propose the protocol to an operator. Optionally, operator feedback may be collected and fed back into the training database 3001 to be considered when retraining the model.

The application system 3000B comprises a processing unit 3010 which may or may not be the same as processing unit 3003. The processing unit 3010 may receive patient related information for a patient to be examined. The patient related information may for example comprise information 3011A descriptive of the patient and referral information 3011B. The patient related information may be used as input for the generated machine learning model (of FIG. 3A) in order to perform a prediction for at least one imaging protocol.

The result comprising the predicted one or more imaging protocols, is presented to the operator, for example on a console screen 3013 of the MRI system or on an additional device. The result may consist of a single recommendation, or a list of proposed protocols. In one example, the operator may be asked to either accept and use any of the proposed protocols, or to reject the choice and select an Examcard or other set of protocol parameters manually.

Optionally, the operator may be asked to explain the decision for not choosing the proposed imaging protocol, for example through a modal dialog window on the screen 3013. For example, the explanation of the operator may indicate that the proposed protocol must not differ from a reference protocol by more than a predefined value. The operator's input is then fed back into the training database 3001 to be included in a subsequent retraining of the machine learning algorithm. In this way, the machine learning algorithm continues to adapt its decisions to clinical practice.

Figure 4:
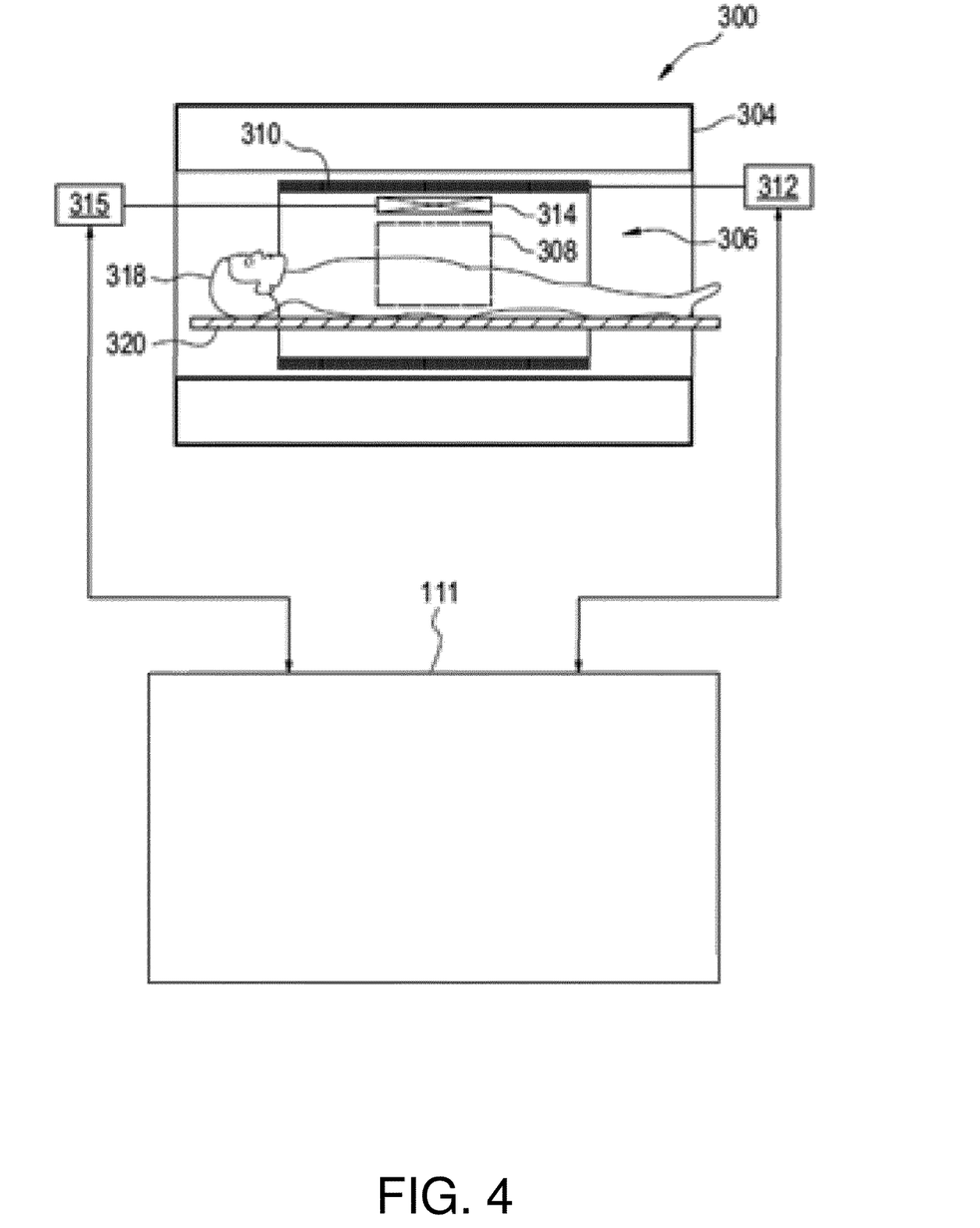
FIG. 4 shows a cross-sectional and functional view of an MRI system.

FIG. 4 illustrates a magnetic resonance imaging system 300 as an example of the medical system 100. The magnetic resonance imaging system 300 comprises a magnet 304. The magnet 304 is a superconducting cylindrical type magnet with a bore 306 in it. The use of different types of magnets is also possible; for instance, it is also possible to use both a split cylindrical magnet and a so called open magnet. A split cylindrical magnet is similar to a standard cylindrical magnet, except that the cryostat has been split into two sections to allow access to the iso-plane of the magnet. Such magnets may for instance be used in conjunction with charged particle beam therapy. An open magnet has two magnet sections, one above the other with a space in-between that is large enough to receive a subject 318 to be imaged, the arrangement of the two sections area similar to that of a Helmholtz coil. Inside the cryostat of the cylindrical magnet there is a collection of superconducting coils. Within the bore 306 of the cylindrical magnet 304 there is an imaging zone or volume or anatomy 308 where the magnetic field is strong and uniform enough to perform magnetic resonance imaging.

Within the bore 306 of the magnet there is also a set of magnetic field gradient coils 310 which is used during acquisition of magnetic resonance data to spatially encode magnetic spins of a target volume within the imaging volume or examination volume 308 of the magnet 304. The magnetic field gradient coils 310 are connected to a magnetic field gradient coil power supply 312. The magnetic field gradient coils 310 are intended to be representative. Typically, magnetic field gradient coils 310 contain three separate sets of coils for the encoding in three orthogonal spatial directions. A magnetic field gradient power supply supplies current to the magnetic field gradient coils. The current supplied to the magnetic field gradient coils 310 is controlled as a function of time and may be ramped or pulsed.

MRI system 300 further comprises an RF coil 314 at the subject 318 and adjacent to the examination volume 308 for generating RF excitation pulses. The RF coil 314 may include for example a set of surface coils or other specialized RF coils. The RF coil 314 may be used alternately for transmission of RF pulses as well as for reception of magnetic resonance signals e.g., the RF coil 314 may be implemented as a transmit array coil comprising a plurality of RF transmit coils. The RF coil 314 is connected to one or more RF amplifiers 315.

The magnetic field gradient coil power supply 312 and the RF amplifier 315 are connected to a hardware interface of control system 111. The memory 107 of control system 111 may for example comprise a control module. The control module contains computer-executable code which enables the processor 103 to control the operation and function of the magnetic resonance imaging system 300. It also enables the basic operations of the magnetic resonance imaging system 300 such as the acquisition of magnetic resonance data.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a 'circuit', 'module' or 'system'. Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

A 'computer memory' or 'memory' is an example of a computer-readable storage medium. A computer memory is any memory which is directly accessible to a processor. A 'computer storage' or 'storage' is a further example of a computer-readable storage medium. A computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising 'a processor' should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the 'C' programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device'. A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word 'comprising' does not exclude other elements or steps, and the indefinite article 'a' or 'an' does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
101 scanning imaging system
103 processor
107 memory
108 power supply
109 bus
111 control system
121 software
125 display
129 user interface
150 AI component
201-205 method steps
300 magnetic resonance imaging system
304 magnet
306 bore of magnet
308 imaging zone
310 magnetic field gradient coils
312 magnetic field gradient coil power supply
314 radio-frequency coil
315 RF amplifier
318 subject.

3000A training system
3000B application system
3001 training database
3002A-C data sources
3003 processing unit
3004 machine learning model
3007 listing
3010 processing unit
3011A-B information
3013 display.

The invention claimed is:

1. A medical imaging method for performing magnetic resonance imaging of a subject using a set of imaging parameters of imaging protocols, the method comprising:
receiving information related to the subject for a specific clinical question;
optimizing at least one imaging protocol using a predefined machine learning model comprising a classification type model or a regression type model operating on the received information for said specific clinical question to produce a suggested imaging protocol, wherein the suggested imaging protocol includes at least part of the set of imaging parameters whose associated values are determined by the optimizing, and wherein the predefined machine learning model is trained on a training set indicative of imaging protocols in association with respective subject information; and
presenting the suggested imaging protocol on a user interface displayed on a display.

2. A non-transitory storage medium storing machine executable instructions stored on the non-transitory computer readable medium for execution by a processor, wherein execution of the machine executable instructions causes the processor to perform the method for performing magnetic resonance imaging of a subject using a set of imaging parameters of imaging protocols, the method comprising:
receiving information related to the subject for a specific clinical question;
optimizing at least one imaging protocol using a predefined machine learning model comprising a classification type model or a regression type model
operating on the received information for said specific clinical question to produce a suggested imaging protocol, wherein the suggested imaging protocol includes at least part of the set of imaging parameters whose associated values are determined by the optimizing, and wherein the predefined machine learning model is trained on a training set indicative of imaging protocols in association with respective subject information; and
presenting the suggested imaging protocol on a user interface displayed on a display.

3. A medical analysis system, comprising: a memory containing machine executable instructions; and a processor for controlling the medical analysis system, wherein execution of the machine executable instructions causes the medical imaging system to:
receive, with the processor, information related for a specific clinical question to a subject;
optimizing at least one imaging protocol using a predefined machine learning model comprising a classification type model or a regression type model operating on the received information for said specific clinical question to produce a suggested imaging protocol, wherein the suggested imaging protocol includes at least part of a set of imaging parameters whose associated values are determined by the optimizing, and wherein the predefined machine learning model is trained on a training set indicative of imaging protocols in association with respective subject information; and presenting the suggested imaging protocol on a user interface displayed on a display.

4. The method of claim 1, further comprising:

prior to the optimizing, training a predefined machine learning algorithm using the training set, thereby generating the machine learning model.

5. The method of claim 4, further comprising generating the training set comprising collecting data from at least one data source, and extracting from the collected data the imaging protocols and associated subject information, wherein the data source comprises at least one of log files of MRI systems and user reports indicative of imaging protocols and subjects imaged using said imaging protocols.

6. The method of claim 4, the training set comprising simulation data that is obtained from a simulation of magnetic resonance imaging of subjects.

7. The method of claim 4, further comprising repeating the suggesting step for other received subject information, and updating the training set using the suggested imaging protocols and the received subject information and repeating the training of the machine learning algorithm using the updated training set.

8. The method of claim 4, wherein each imaging protocol of the training set is associated with a quality score indicative of the quality of images that can be obtained from an imaging using each imaging protocol, wherein the training set comprises the quality scores.

9. The method of claim 8, wherein the quality score comprises at least one of: image quality of the obtainable images, the number of user interventions when using the imaging protocol, number of MR repeat scans when using the imaging protocol, delays and idle times and their distribution when using the imaging protocol.

10. The method of claim 1, further comprising determining the difference between the provided imaging protocol and a predefined reference imaging protocol of a protocol database, and updating the protocol database based on the determined difference.

11. The method of claim 1, wherein the subject related information comprises a description of the subject and/or clinical use case of the subject.

12. The method of claim 1, wherein the suggesting comprises predicting the imaging protocol using the subject information.

13. The method of claim 1, further comprising receiving values for the set of imaging parameters, the suggesting comprising:

predicting a quality score for the received set of imaging parameters and the subject information, wherein the imaging parameters of the suggested imaging protocol are the received set of parameters if the predicted quality score is higher than a predefined threshold; or adjusting the received set of parameters if the predicted quality score is smaller than the predefined threshold, wherein the imaging parameters of the suggested imaging protocol are the adjusted parameters.

14. The medical analysis system of claim 3, being configured to connect to multiple MRI systems and to receive log files of the MRI systems.

15. A MRI system comprising the medical analysis system of claim 3, the MRI system being configured for acquiring image data using an imaging protocol provided by the medical analysis system.

* * * * *